United States Patent [19]

Ishikawa et al.

[11] Patent Number: 5,389,620

[45] Date of Patent: Feb. 14, 1995

[54] ENDOTHELIN ANTAGONISTIC HETEROAROMATIC RING-FUSED CYCLOPENTENE DERIVATIVES

[75] Inventors: Kiyofumi Ishikawa; Toshio Nagase; Toshiaki Mase; Takashi Hayama; Masaki Ihara; Masaru Nishikibe; Mitsuo Yano, all of Tsukuba, Japan

[73] Assignee: Banyu Pharmaceutical Co., Ltd., Tokyo, Japan

[21] Appl. No.: 165,880

[22] Filed: Dec. 14, 1993

[30] Foreign Application Priority Data

Aug. 18, 1993 [JP] Japan .................. 5-225100
Oct. 15, 1993 [JP] Japan .................. 5-281613
Oct. 21, 1993 [JP] Japan .................. 5-285677

[51] Int. Cl.⁶ .................. A61K 31/435; C07D 221/04
[52] U.S. Cl. .................. 514/80; 514/248; 514/249; 514/258; 514/299; 544/232; 544/235; 544/244; 544/253; 544/337; 544/349; 546/112; 546/183; 548/152; 548/180
[58] Field of Search .............. 546/112, 183; 514/299, 514/248, 249, 258, 80; 544/235, 253, 337, 349, 232, 244; 548/152, 180

[56] References Cited

FOREIGN PATENT DOCUMENTS 9308799  5/1993  WIPO .

*Primary Examiner*—Bernard Dentz
*Attorney, Agent, or Firm*—Oblon, Spivak, McClelland, Maier & Neustadt

[57] ABSTRACT

A heteroaromatic ring-fused cyclopentene derivative of the formula:

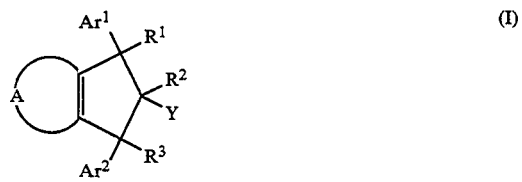

wherein the variables are as defined in the specification; or a pharmaceutically acceptable salt thereof.

5 Claims, No Drawings

ENDOTHELIN ANTAGONISTIC HETEROAROMATIC RING-FUSED CYCLOPENTENE DERIVATIVES

The present invention relates to novel heteroaromatic ring-fused cyclopentene derivatives having antagonism against three endothelin isopeptides (endothelin-1, endothelin-2 and endothelin-3), which are physiologically highly active endogenous peptides, processes for their preparation and their use as a drug.

Two endothelin receptor subtypes $ET_A$ and $ET_B$ are known so far. The compounds of the present invention possess high affinity to at least one of these two receptor subtypes, thereby inhibiting vasoconstriction and bronchoconstriction induced by the endothelins. The compounds of the present invention provide a new therapeutic potential, particularly for the treatment of hypertension, pulmonary hypertension, Raynaud's disease, acute renal failure, myocardial infarction, angina pectoris, cerebral infarction, cerebral vasospasm, arteriosclerosis, asthma, gastric ulcer, diabetes, restenosis, endotoxin shock, endotoxin-induced multiple organ failure or disseminated intravascular coagulation, and/or cyclosporin-induced renal failure or hypertension.

Endothelin is a polypeptide composed of 21 amino acids, and it is produced by vascular endothelial cells of human or pig. Endothelin has a potent vasoconstrictor effect and a sustained and potent pressor action (Nature, 332, 411–415 (1988)).

Three endothelin isopeptides (endothelin-1, endothelin-2 and endothelin-3), which resemble one another in structure, exist in the bodies of animals including human, and these peptides have vasoconstriction and pressor effects (Proc. Natl. Acad, Sci, USA, 86, 2863–2867 (1989)).

As reported, the endothelin levels are clearly elevated in the blood of patients with essential hypertension, acute myocardial infarction, pulmonary hypertension, Raynaud's disease, diabetes or atherosclerosis, or in the washing fluids of the respiratory tract or the blood of patients with asthmaticus as compared with normal levels (Japan, J. Hypertension, 12, 79, (1989), J. Vascular Medicine Biology, 2, 207 (1990), Diabetologia, 33, 306–310 (1990), J. Am. Med. Association, 264, 2868 (1990), and The Lancet, ii, 747–748 (1989) and ii, 1144–1147 (1990)).

Further, an increased sensitivity of the cerebral blood vessel to endothelin in an experimental model of cerebral vasospasm (Japan. Soc. Cereb. Blood Flow & Metabol., 1, 73 (1989)), an improved renal function by the endothelin antibody in an acute renal failure model (J. Clin, Invest., 83, 1762–1767 (1989), and inhibition of gastric ulcer development with an endothelin antibody in a gastric ulcer model (Extract of Japanese Society of Experimental Gastric Ulcer, 50 (1991)) have been reported. Therefore, endothelin is assumed to be one of mediators causing acute renal failure or cerebral vasospasm following subarachnoid hemorrhage.

Further, endothelin is secreted not only by endothelial cells but also by tracheal epithelial cells or from kidney cells (FEBS Letters, 255, 129–132 (1989), and FEBS Letters, 249, 42–46 (1989)).

Endothelin was also found to control the release of physiologically active endogenous substances such as renin, atrial natriuretic peptide, endothelium-derived relaxing factor (EDRF), thromboxane $A_2$, prostacyclin, noradrenaline, angiotensin II and substance P (Biochem. Biophys, Res. Commun., 157, 1164–1168 (1988); Biochem. Biophys, Res. Commun., 155, 167–172 (1989); Proc. Natl. Acad. Sci. USA, 85, 9797–9800 (1989); J. Cardiovasc. Pharmacol., 13, S89–S92 (1989); Japan. J. Hypertension, 12, 76 (1989) and Neuroscience Letters, 102, 179–184 (1989)). Further, endothelin causes contraction of the smooth muscle of gastrointestinal tract and the uterine smooth muscle (FEBS Letters, 247, 337–340 (1989); Eur. J. Pharmacol., 154, 227–228 (1988); and Biochem. Biophys. Res. Commun., 159, 317–323 (1989)). Further, endothelin was found to promote proliferation of rat vascular smooth muscle cells, suggesting a possible relevance to the arterial hypertrophy (Atherosclerosis, 78, 225–228 (1989)). Furthermore, since the endothelin receptors are present in a high density not only in the peripheral tissues but also in the central nervous system, and the cerebral administration of endothelin induces a behavioral change in animals, endothelin is likely to play an important role for controlling nervous functions (Neuroscience Letters, 97, 276–279 (1989)). Particularly, endothelin is suggested to be one of mediators for pain (Life Sciences, 49, PL61–PL65 (1991)).

On the other hand, endotoxin is one of potential candidates to promote the release of endothelin. Remarkable elevation of the endothelin levels in the blood or in the culture supernatant of endothelial cells was observed when endotoxin was exogenously administered to animals or added to the culture endothelial cells, respectively. These findings suggest that endothelin is one of important mediators for endotoxin-induced diseases (Biochem. Biophys. Res. Commun., 161, 1220–1227 (1989); and Acta Physiol. Scand., 137, 317–318 (1989)).

Further, it was reported that cyclosporin remarkably increased endothelin secretion in the renal cell culture (LLC-PK1 cells) (Eur. J. Pharmacol., 180, 191–192 (1990)). Further, dosing of cyclosporin to rats reduced the glomerular filtration rate and increased the blood pressure in association with a remarkable increase in the circulating endothelin level. This cyclosporin-induced renal failure can be suppressed by the administration of endothelin antibody (Kidney Int., 37, 1487–1491 (1990)). Thus, it is assumed that endothelin is significantly involved in the pathogenesis of the cyclosporin-induced diseases.

Such various effects of endothelin are caused by the binding of endothelin to endothelin receptors widely distributed in many tissues (Am. J. Physiol., 256, R856–R866 (1989)).

It is known that vasoconstriction by the endothelins is caused via at least two subtypes of endothelin receptors (J. Cardiovasc. Pharmacol., 17(Suppl.7), S119–S121 (1991)). One of endothelin receptors is $ET_A$ receptor selective to ET-1 rather than ET-3, and the other is $ET_B$ receptor equally active to ET-1 and ET-3. These receptor proteins are reported to be different from each other (Nature, 348, 730–735 (1990)).

These two subtypes of endothelin receptors are differently distributed in tissues. It is known that the $ET_A$ receptor is present mainly in cardiovascular tissues, whereas the $ET_B$ receptor is widely distributed in various tissues such as brain, kidney, lung, heart and vascular tissues.

Substances which specifically inhibit the binding of endothelin to the endothelin receptors are believed to antagonize various pharmacological activities of endothelin and to be useful as a drug in a wide field. Since, the action of the endothelins is caused via not only the $ET_A$ receptor but also the $ET_B$ receptor, novel non-peptidic substances with ET receptor antagonistic activity to either receptor subtype are desired to block activities of the endothelins effectively in various diseases.

Endothelin is an endogenous substance which directly or indirectly (by controlling liberation of various endogenous substances) induces sustained contraction of vascular or non-vascular smooth muscles, and its excess production or excess secretion is believed to be one of pathogeneses for hypertension, pulmonary hypertension, Raynaud's disease, bronchial asthma, gastric ulcer, diabetes, arteriosclerosis, restenosis, acute renal failure, myocardial infarction, angina pectoris, cerebral vasospasm and cerebral infarction. Further, it is suggested that endothelin serves as an important mediator involved in diseases such as endotoxin shock, endotoxin-induced multiple organ failure or disseminated intravascular coagulation, and/or cyclosporin-induced renal failure or hypertension. Two endothelin receptors $ET_A$ and $ET_B$ are known so far. An antagonistic agent against the $ET_B$ receptor as well as the $ET_A$ receptor is useful as a drug. In the field of anti-endothelin agents, some non-peptidic compounds possessing antagonistic activity against endothelin receptors were already disclosed in patents (for example, EP 0526708 A1, WO 93/08799 A1). Accordingly, it is an object of the present invention to provide a novel therapeutics for the treatment of the above-mentioned various diseases by an invention of a novel and potent non-peptidic antagonist against either $ET_A$ or $ET_B$ receptor.

In order to accomplish the above object, the present inventors have synthesized various non-peptidic derivatives and have investigated their endothelin antagonistic activities, and as a result have found that novel heteroaromatic ring-fused cyclopentene derivatives represented by the following formula (I) and their pharmaceutically acceptable salts have potent affinity to at least one of these $ET_A$ and $ET_B$ receptor subtypes. The present invention has been accomplished on the basis of this discovery.

Thus, the present invention provides a non-peptidic derivative of the formula:

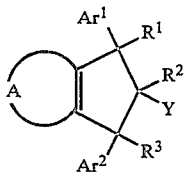

(I)

wherein each of $Ar^1$ and $Ar^2$ is independently a phenyl group or a thienyl group wherein an optional hydrogen atom(s) on the aromatic ring may be replaced with 1 to 4 groups selected from the group consisting of a hydroxyl group, a carboxyl group, a $C_1-C_6$ alkoxy carbonyl group, a mono- or di- $C_1-C_6$ alkylaminocarbonyl group, a carbamoyl group, a tetrazol-5-yl group, a methylenedioxy group, a $C_1-C_6$ alkoxy group, a $C_1-C_6$ alkyl group and a $C_2-C_6$ alkenyl group (provided that the $C_1-C_6$ alkoxy group, the $C_1-C_6$ alkyl group and the $C_2-C_6$ alkenyl group may be substituted by a hydroxyl group, an amino group, a mono- or di- $C_1-C_6$ alkylamino group, a $C_1-C_6$ alkoxy carbonyl group, a mono- or di- $C_1-C_6$ alkylaminocarbonyl group, a carbamoyl group, a carboxyl group, a tetrazol-5-yl group, a 2-oxo-3H-1,2,3,5-oxathiadiazol-4-yl group, a 2.2-dioxo-3H-1,2,3,5-oxathiadiazol-4-yl group, or a 5-oxo-4H-1,2,4-oxadiazol-3-yl group); each of $R^1$, $R^2$ and $R^3$ is independently a hydrogen atom, a hydroxyl group or a $C_1-C_6$ alkyl group, or $R^1$ and $R^2$, or $R^2$ and $R^3$ together form a single bond; Y is a group of —CO—$R^4$ (wherein $R^4$ is a hydroxyl group, an amino group, a $C_1-C_6$ alkoxy group, a mono- or di- $C_1-C_6$ alkylamino group, an arylsulfonylamino group wherein an optional hydrogen atom(s) on the aryl ring may be replaced with a $C_1-C_6$ alkyl group, or a $C_1-C_6$ alkylsulfonylamino group which may be substituted by an aryl group on the alkyl moiety), a sulfo group, a phosphono group, a tetrazol-5-yl group, a 2-oxo-3H-1,2,3,5-oxathiadiazol-4-yl group, a 2.2-dioxo-3H-1,2,3,5-oxathiadiazol-4-yl group, or a 5-oxo-4H-1,2,4-oxadiazol-3-yl group; and A is a group which forms together with the adjacent carbon-carbon double bond a 5- or 6- membered heteroaromatic ring including 1 to 4 hetero atoms selected from the group consisting of a nitrogen atom, an oxygen atom and a sulfur atom (provided that an optional hydrogen atom(s) on the heteroaromatic ring may be replaced with a hydroxyl group, an amino group, a $C_1-C_6$ alkoxy group, a halogen atom, a cyano group, a nitro group, a mono- or di- $C_1-C_6$ alkylamino group, a carboxyl group, a $C_1-C_6$ alkoxycarbonyl group, a $C_1-C_6$ acyl group, an aroyl group, or a $C_1-C_6$ alkyl group, $C_2-C_6$ alkenyl group or $C_2-C_6$ alkynyl group which may be substituted by a $C_1-C_6$ alkoxy group or a $C_1-C_6$ alkylamino group, and when the heteroaromatic ring includes one or more nitrogen atoms, the nitrogen atom(s) may be oxidized to form an N-oxide group); or a pharmaceutically acceptable salt thereof.

Now, the present invention will be described in further detail with reference to the preferred embodiments.

Now, the meanings of various abbreviations used in this specification will be given.

| Abbreviation | Meaning of Abbreviation |
|---|---|
| Et | ethyl |
| Me | methyl |
| $^n$Pr | n-propyl |
| $^i$Pr | isopropyl |
| $^n$Bu | n-butyl |
| $^t$Bu | tert-butyl |
| Ph | phenyl |
| Bzl | benzyl |
| c-Pent | cyclopentyl |
| CDI | 1,1'-carbonyldiimidazole |
| DCC | N,N'-dicyclohexylcarbodiimide |
| DMAP | 4-(dimethylamino)pyridine |
| AcOEt | ethyl acetate |
| DMF | N,N-dimethylformamide |
| DMSO | dimethylsulfoxide |
| HMPA | hexamethylphosphoric triamide |
| NMP | N-methylpyrrolidone |
| NMM | N-methylmorpholine |
| EDCI.HCl | 1-ethyl-3-(3-dimethylaminopropyl)-carbodiimide.hydrochloride |
| HOBT.H$_2$O | 1-hydroxy-1H-benzotriazole monohydrate |
| HOSu | N-hydroxysuccinimide |
| LDA | lithium diisopropylamide |
| mCPBA | m-chloroperbenzoic acid |
| TEA | triethylamine |
| TFA | trifluoro acetic acid |
| THF | tetrahydrofuran |
| TsOH | p-toluene sulfonic acid |
| Ts | p-toluenesulfonyl |
| Z | benzyloxycarbonyl |
| MOPS | 3-morpholinopropane sulfonic acid |
| HEPES | 2-[4-(2-hydroxyethyl)-1-piperazinyl]-ethane sulfonic acid |
| Tris | tris(hydroxymethyl)aminomethane |

| Abbreviation | Meaning of Abbreviation |
| --- | --- |
| PMSF | phenylmethanesulfonyl fluoride |

Now, the definitions of the various terms mentioned in this specification will be explained.

In this specification, the $C_1$–$C_6$ alkyl group means a linear or branched alkyl group having 1 to 6 carbon atoms such as a methyl, ethyl, propyl, isopropyl, butyl, isobutyl, sec-butyl, tert-butyl, pentyl, isopentyl, neopentyl, tert-pentyl, 1-methylbutyl, 2-methylbutyl, 1,2-dimethylpropyl, 1-ethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl or 1-ethyl-1-methylpropyl group.

The $C_1$–$C_6$ alkoxy group means a linear or branched alkoxy group having 1 to 6 carbon atoms such as a methoxy, ethoxy, propoxy, isopropoxy, butoxy, isobutoxy, sec-butoxy, tert-butoxy, pentyloxy or hexyloxy group.

The $C_2$–$C_6$ alkenyl group means a linear or branched alkenyl group having 2 to 6 carbon atoms such as a vinyl, allyl, 2-propenyl, isopropenyl, 3-butenyl, 2-butenyl, 1-butenyl, 1-methyl-2-propenyl, 1-methyl-1-propenyl, 1-ethyl-1-ethenyl, 2-methyl-2-propenyl, 2-methyl-1-propenyl or 4-pentenyl group.

The $C_2$–$C_6$ alkynyl group means a linear or branched alkynyl group having 2 to 6 carbon atoms such as a ethynyl, 1-propynyl, 2-propynyl, 1-butynyl, 2-butynyl, 3-butynyl, 1-methyl-2-propynyl or 1-pentynyl group.

The aryl group means a cyclohydrocarbonic or heterocyclic aromatic group such as a phenyl, naphthyl, thienyl, pyridyl or furyl group.

The halogen atom means a fluorine, chlorine, bromine or iodine atom.

The $C_1$–$C_6$ acyl group means a linear or branched acyl group having 1 to 6 carbon atoms such as a formyl, acetyl, propionyl or isopropionyl group.

The aroyl group may, for example, be a benzoyl, thienylcarbonyl, pyridylcarbonyl or furylcarbonyl group.

Now, this invention will be described in more detail with reference to specific examples for the various symbols used in the formula (I).

In $Ar^1$ and $Ar^2$, examples of the phenyl group or the thienyl group wherein an optional hydrogen atom(s) on the aromatic ring may be replaced with 1 to 4 groups selected from the group consisting of a hydroxyl group, a carboxyl group, a $C_1$–$C_6$ alkoxy carbonyl group, a mono- or di- $C_1$–$C_6$ alkylaminocarbonyl group, a carbamoyl group, a tetrazol-5-yl group, a methylenedioxy group, a $C_1$–$C_6$ alkoxy group, a $C_1$–$C_6$ alkyl group and a $C_2$–$C_6$ alkenyl group (provided that the $C_1$–$C_6$ alkoxy group, the $C_1$–$C_6$ alkyl group and the $C_2$–$C_6$ alkenyl group may be substituted by a hydroxyl group, an amino group, a mono- or di- $C_1$–$C_6$ alkylamino group, a $C_1$–$C_6$ alkoxy carbonyl group, a mono- or di- $C_1$–$C_6$ alkylaminocarbonyl group, a carbamoyl group, a carboxyl group, a tetrazol-5-yl group, a 2-oxo-3H-1,2,3,5-oxathiadiazol-4-yl group, a 2,2-dioxo-3H-1,2,3,5-oxathiadiazol-4-yl group, or a 5-oxo-4H-1,2,4-oxadiazol-3-yl group) are phenyl, thienyl, 2-hydroxyphenyl, 3-hydroxyphenyl, 4-hydroxyphenyl, 2-carboxyphenyl, 3-carboxyphenyl, 4-carboxyphenyl, 2-hydroxymethylphenyl, 3-hydroxymethylphenyl, 4-hydroxymethylphenyl, 2-(tetrazol-5-yl)phenyl, 3-(tetrazol-5-yl)phenyl, 4-(tetrazol-5-yl)phenyl, 2,3-methylenedioxyphenyl, 3,4-methylenedioxyphenyl, 2-methoxyphenyl, 3-methoxyphenyl, 4-methoxyphenyl, 2-ethoxyphenyl, 3-ethoxyphenyl, 4-ethoxyphenyl, 2-propoxyphenyl, 3-propoxyphenyl, 4-propoxyphenyl, 2-butoxyphenyl, 3-butoxyphenyl, 4-butoxyphenyl, 2,3-dimethoxyphenyl, 3,4-dimethoxyphenyl, 2,4-dimethoxyphenyl, 2,5-dimethoxyphenyl, 2,6-dimethoxyphenyl, 3,5-dimethoxyphenyl, 2,3,4-trimethoxyphenyl, 3,4,5-trimethoxyphenyl, 2,3-methylenedioxy-4-methoxyphenyl, 2,3-methylenedioxy-5-methoxyphenyl, 2,3-methylenedioxy-6-methoxyphenyl, 3,4-methylenedioxy-2-methoxyphenyl, 3,4-methylenedioxy-5-methoxyphenyl, 3,4-methylenedioxy-6-methoxyphenyl, 2-tolyl, 3-tolyl, 4-tolyl, 2-ethylphenyl, 3-ethylphenyl, 4-ethylphenyl, 2-propylphenyl, 3-propylphenyl, 4-propylphenyl, 2-vinylphenyl, 3-vinylphenyl, 4-vinylphenyl, 2-(1-propenyl)phenyl, 3-(1-propenyl)phenyl, 4-(1-propenyl)phenyl, 2-hydroxy-4-methoxyphenyl, 3-hydroxy-4-methoxyphenyl, 3-hydroxy-2-methoxyphenyl, 4-hydroxy-2-methoxyphenyl, 5-hydroxy-2-methoxyphenyl, 6-hydroxy-2-methoxyphenyl, 2-hydroxy-3-methoxyphenyl, 4-hydroxy-3-methoxyphenyl, 2-(2-aminoethoxy)-4-methoxyphenyl, 3-(2-aminoethoxy)-4-methoxyphenyl, 2-(2-methylaminoethoxy)-4-methoxyphenyl, 3-(2-methylaminoethoxy)-4-methoxyphenyl, 2-(2-dimethylaminoethoxy)-4-methoxyphenyl, 3-(2-dimethylaminoethoxy)-4-methoxyphenyl, 2-(2-hydroxyethoxy)phenyl, 3-(2-hydroxyethoxy)phenyl, 4-(2-hydroxyethoxy)phenyl, 2-(2-hydroxyethoxy)-4-methoxyphenyl, 3-(2-hydroxyethoxy)-4-methoxyphenyl, 2-carboxymethoxy-4-methoxyphenyl, 3-carboxymethoxy-4-methoxyphenyl, 2-(tetrazol-5-ylmethoxy)-4-methoxyphenyl, 3-(tetrazol-5-ylmethoxy)-4-methoxyphenyl, 2-(2-oxo-3H-1,2,3,5-oxathiazol-4-ylmethoxy)-4-methoxyphenyl, 3-(2-oxo-3H-1,2,3,5-oxathiazol-4-ylmethoxy)-4-methoxyphenyl, 2-(2,2-dioxo-3H-1,2,3,5-oxathiadiazol-4-ylmethoxy)-4-methoxyphenyl, 3-(2,2-dioxo-3H-1,2,3,5-oxathiadiazol-4-ylmethoxy)-4-methoxyphenyl, 2-(5-oxo-4H-1,2,4-oxadiazol-3-ylmethoxy)-4-methoxyphenyl, 3-(5-oxo-4H-1,2,4-oxadiazol-3-ylmethoxy)-4-methoxy phenyl,2-carboxymethoxy-3,4-methylenedioxyphenyl, 5-carboxymethoxy-3,4-methylenedioxyphenyl, 6-carboxymethoxy-3,4-methylenedioxyphenyl, 2-(tetrazol-5-ylmethoxy)-3,4-methylenedioxyphenyl, 5-(tetrazol-5-ylmethoxy)-3,4-methylenedioxyphenyl, 6-(tetrazol-5-ylmethoxy)-3,4-methylenedioxyphenyl, 2-hydroxymethyl-4-methoxyphenyl, 3-hydroxymethyl-4-methoxyphenyl, 2-(2-hydroxyethyl)-4-methoxyphenyl, 3-(2-hydroxyethyl)-4-methoxyphenyl, 2-(2-carboxyethyl)-4-methoxyphenyl, 3-(2-carboxyethyl)-4-methoxyphenyl, 2-(2-carboxyethenyl)-4-methoxyphenyl, 3-(2-carboxyethenyl)-4-methoxyphenyl, 2-(2-tetrazol-5-ylethyl)-4-methoxyphenyl and 3-(2-tetrazol-5-ylethyl)-4-methoxyphenyl groups.

In $R^1$, $R^2$ and $R^3$, examples of the $C_1$–$C_6$ alkyl group are methyl, ethyl and propyl groups.

In $R^4$, examples of the mono- or di- $C_1$–$C_6$ alkylamino group are methylamino, dimethylamino, ethylamino, diethylamino and propylamino groups.

In $R^4$, examples of the arylsulfonylamino group wherein an optional hydrogen atom(s) on the aryl ring may be replaced with $C_1$–$C_6$ alkyl groups are benzenesulfonylamino, 4-toluenesulfonylamino, 4-isopropylbenzenesulfonylamino, 4-tert-butylbenzenesulfonylamino and 2-thiophenesulfonylamino groups.

In $R^4$, examples of the $C_1$–$C_6$ alkylsulfonylamino group which may be substituted by an aryl group on the alkyl moiety are methanesulfonylamino, ethanesulfonylamino, phenylmethanesulfonylamino and thienylmethanesulfonylamino groups.

A forms together with the adjacent carbon-carbon double bond a 5- or 6- membered heteroaromatic ring including 1 to 4 hetero atoms selected from the group consisting of a nitrogen atom, an oxygen atom and a sulfur atom, such as, for example, furan, pyrrole, thiophene, diazole, thiazole, oxazole, pyridine, pyrimidine, pyrazine, pyridazine, pyrimidine, pyridazine, pyrazine or triazine ring.

Preferred compounds are those wherein $Ar^1$ and $Ar^2$ are independently a phenyl group, a thienyl group and the said group wherein an optional hydrogen atom(s) on s the aromatic ring is replaced with 1 to 4 groups selected from the group consisting of a hydroxyl group, a $C_1$–$C_6$ alkoxy group, a methylenedioxy group, a hydroxy $C_2$–$C_6$ alkoxy group, a carboxy $C_1$–$C_6$ alkoxy group, a $C_1$–$C_6$ alkylamino $C_2$–$C_6$ alkoxy group, a tetrazol-5-yl $C_1$–$C_6$ alkoxy group, a 2-oxo-3H-1,2,3,5-oxathiadiazol-4-yl $C_1$–$C_6$ alkoxy group, a 2,2-dioxo-3-1,2,3,5-oxathiadiazol-4-yl $C_1$–$C_6$ alkoxy group, a 5-oxo-4-1,2,4-oxadiazol-3-yl $C_1$–$C_6$ alkoxy group, a hydroxy $C_1$–$C_6$ alkyl group, a carboxy $C_1$–$C_6$ alkoxy group; and A is a group which forms together with the adjacent carbon-carbon double bond a substituted or unsubstituted furan, pyrrole, thiophene, diazole, thiazole, oxazole, pyridine, diazine or triazine ring, or the said heteroaromatic ring N-oxide.

More preferred compounds are those wherein A is a group which forms together with the adjacent carbon-carbon double bond a substituted or unsubstituted pyridine, pyrimidine, pyridadine, pyrazine or thiazole ring, or the said heteroaromaic ring N-oxide.

Most preferred compounds are those wherein A is a group which forms together with the adjacent carbon-carbon double bond a pyridine ring (provided that an optional hydrogen atom(s) on the pyridine ring may be replaced with a $C_1$–$C_6$ alkyl group, a $C_1$–$C_6$ alkoxy group, a $C_1$–$C_6$ alkoxy $C_1$–$C_6$ alkyl group, a mono- or di- $C_1$–$C_6$ alkylamino $C_1$–$C_6$ alkyl group); $R^1$ and $R^3$ are a hydrogen atom or a hydroxy group and $R^2$ is a hydrogen atom, or one of $R^1$ and $R^3$ is a hydrogen atom and the other together with $R^2$ is a single bond; the stereochemistry of $Ar^1$ and Y, and $Ar^2$ and Y are trans.

The present invention provides novel heteroaromatic ring-fused cyclopentene derivatives of Formula (I) above

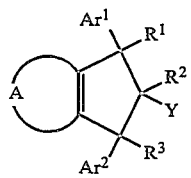

which can be prepared by a process which comprises:
1) reacting a β-keto ester derivative of Formula (II):

wherein R is a $C_1$–$C_6$ alkyl group, and $A^1$ is A or its synthetic equivalents, with an aldehyde of Formula (III):

$$Ar^{21}\text{—CHO} \qquad (III)$$

wherein $Ar^{21}$ is $Ar^2$ or its synthetic equivalents, in a suitable solvent such as benzene or toluene with a catalyst such as piperidinium acetate at $-20°$ C. to reflux temperature of a solvent to provide a 2-propenate derivative of Formula (IV):

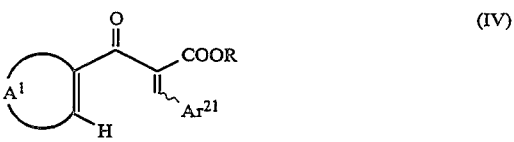

wherein $Ar^{21}$ $A^1$ and R are as defined before.

Cyclization of Compound (IV) in the presence of a suitable Lewis acid such as titanium tetrachloride, tin tetrachloride or aluminum chloride, or alternatively a protic acid such as trifluoroacetic acid, conc. $H_2SO_4$, perchloric acid or polyphosphoric acid in a suitable solvent such as benzene or toluene at $-20°$ C. to reflux temperature of a solvent, provides a cyclopentene derivative of Formula (V):

wherein $Ar^{21}$, $A^1$ and R are as defined before. Dehydrogenation of Compound (V) with 2,3-dichloro-5,6-dicyano-1,4-benzoquinone in an appropriate solvent or alternative bromination of Compound (V) with pyridinium hydrobromide perbromide in dichloromethane followed by treatment with 1,5-diazabicyclo[4.3.0]non-5-ene provides a cyclopentadienone derivative of Formula (VI):

wherein $Ar^{21}$, $A^1$ and R are as defined before.
2) Alternatively, a compound of Formula (VI) can be prepared as follows:
a compound of Formula (VII):

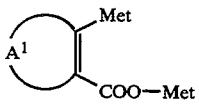

wherein Met is metal and $A^1$ is as defined before, which was prepared by halogen-metal exchange reaction of the corresponding β-halocarboxylic acid with 2 equivalents of a metal reagent such as butyllithium, or by direct metallation of a β-hydrogen of the corresponding carboxylic acid with 2 equivalents of a strong base such as tert-butyllithium, sodium or lithium, was treated with aroyl halide or arylnitrile in an aprotic solvent such as THF, $Et_2O$ or dimethoxyethane at $-100°$ C. to room temperature to provide a carboxylic acid derivative of Formula (VIII):

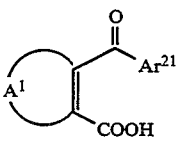

wherein $Ar^{21}$ and $A^1$ are as defined before.

To activate the carboxyl group, Compound (VIII) can be treated with a halogenated agent such as thionyl chloride or oxalyl chloride at $-40°$ C. to $100°$ C. or with CDI in an aprotic solvent such as $CHCl_3$, THF or DMF at $-20°$ C. to room temperature. The resulting activated carboxylic acid derivative, that is, acid chloride or imidazolide, can then be treated with 1 to 5 equivalents of diethyl magnesium malonate, magnesium salt of malonic acid half ester or lithium enolate of acetic acid ester in a suitable solvent such as ether or THF at $-100°$ C. to $50°$ C. to give a compound of Formula (IX):

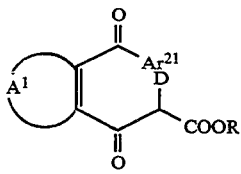

wherein D is H, —COOR, —COOMet or —COOH, and $Ar^{21}$ $A^1$, R and Met are as defined before.

Treatment of Compound (IX) with an aqueous inorganic base such as 5% aqueous sodium carbonate under reflux conditions, or with an acid such as 1N HCl, acetic acid or $SiO_2$ at $0°$ C. to room temperature gives a compound of Formula (VI).

Alternatively, Compound (VIII) can be prepared by reaction of a dicarboxylic acid anhydride of Formula (X):

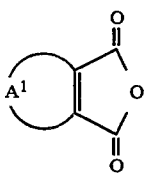

wherein $A^1$ is as defined before, or a dicarboxylic acid mono ester of Formula (XI):

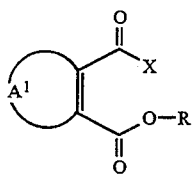

wherein X is a leaving group, and $A^1$ and R are as defined before, with an organometallic reagent of Formula (XII):

wherein $Ar^{21}$ and Met are as defined before, in an aprotic solvent such as THF or ether at $-100°$ C. to room temperature. Preferred organometallic reagents are organomagnesium reagents such as Grignard reagents or organolithium reagents.

3) Treatment of Compound (VI) with an organometallic reagent such as Grignard reagent or organolithium reagent of Formula (XIII):

wherein $Ar^{11}$ and Met are defined before, in a suitable solvent such as THF, $Et_2O$ or dimethoxyethane at $-100°$ C. to room temperature provides compounds of Formula (XIV):

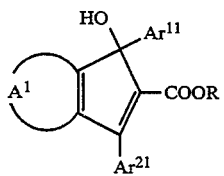

wherein $Ar^{11}$, $Ar^{21}$, $A^1$ and R are as defined before.

Saponification of Compound (XIV) using an inorganic base such as NaOH or KOH in an aqueous solvent such as methanol, ethanol, dioxane or acetonitrile, as the case is required, combined with the following procedures: i) appropriate conversion(s) of a synthetic equivalent(s) to a desired group(s), ii) deprotection of a protective group(s), affords compounds of the present invention which have a hydroxy group as $R^1$ or $R^2$ in Formula (I).

Reduction of Compound (XIV) with a reductant such as triethylsilane in the presence of a Leuis acid such as boron trifluoride etherate in a suitable solvent such as dichloromethane at $-20°$ C. to room temperature; or saponification of Compound (XIV) followed by reduction of a hydroxyl group and re-esterification of a carboxyl group affords an α,β-unsaturated ester of Formula (XV):

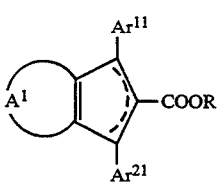

wherein Ar¹¹, Ar²¹, A¹ and R are as defined before. Conjugate addition of an organometallic reagent of Formula (XVI):

$$R^{11}-Met \quad (XVI)$$

wherein $R^{11}$ is a $C_1$-$C_6$ alkyl group, and Met is as defined before, to Compound (XV), followed by appropriate conversion(s) of a synthetic equivalent(s) to a desired group(s) and/or deprotection of a protective group(s), as the case is required, affords compounds of the present invention which are shown in Formula (XVII):

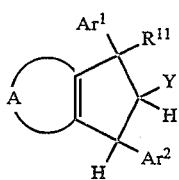
(XVII)

wherein Ar¹, Ar², A, $R^{11}$ and Y are as defined before.

Re-introduction of a double bond into an ester obtained by reacting Compounds (XV) with Compounds (XVI) followed by conjugate addition of another organometallic reagent of Formula (XVIII):

$$R^{31}-Met \quad (XVIII)$$

wherein $R^{31}$ is a $C_1$-$C_6$ alkyl group, and Met is as defined before, and subsequent appropriate conversion affords compounds of the present invention of Formula (XIX):

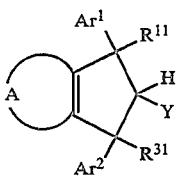
(XIX)

wherein Ar¹, Ar², A, $R^{11}$, $R^{31}$ and Y are as defined before.

Hydrogenation of Compound (XV) with hydrogen gas under pressure at approximately 1-5 kg/cm² in the presence of a suitable catalyst such as 10% palladium on charcoal in a suitable solvent such as ethyl acetate or methanol containing a suitable acid such as acetic acid, conc-H₂SO₄ or perchloric acid, affords compounds of Formula (XX):

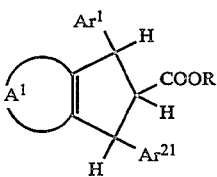
(XX)

wherein Ar¹¹, Ar²¹, A¹ and R are as defined before, which are converted to compounds of the present invention of Formula (XXI):

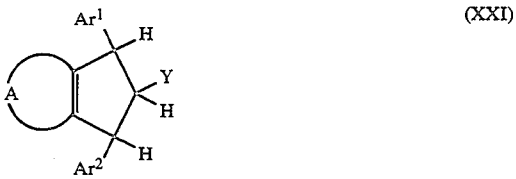
(XXI)

wherein Ar¹, Ar², A and Y are as defined before, by appropriate reaction(s) such as saponification of an ester group, conversion of a synthetic equivalent(s) to a desired functional or substituted group(s), or deprotection of a protective group(s).

Treatment of Compounds (XVII), (XIX) and their synthetic precursors, or Compound (XX) with a compound of Formula (XXII):

$$R^{21}-X \quad (XXII)$$

wherein $R^{21}$ is a $C_1$-$C_6$ alkyl group and X is a leaving group, in the presence of a strong base such as BuLi, LDA or NaH in a suitable solvent such as THF, Et₂O, DMF or DMSO at −100° C. to 100° C. followed by appropriate conversion(s) affords compounds of the present invention of Formula (XXIII):

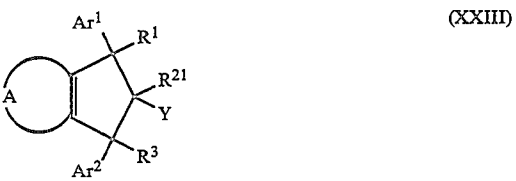
(XXIII)

wherein Ar¹, Ar², A, $R^1$, $R^{21}$, $R^3$ and Y are as defined before.

4) Treatment of Compound (V) with a sulfonic acid anhydride such as trifluoromethanesulfonic acid anhydride in the presence of a strong base such as BuLi or LDA, an organic base such as TEA, or a metal hydride such as NaH, in a suitable solvent such as THF, Et₂O, dimethoxyethane, DMF or DMSO at −78° C. to room temperature affords the corresponding sulfonyloxycyclopentadiene derivatives, which was allowed to react with an organometallic reagent of Formula (XXIV):

$$Ar^{11}-Met \quad (XXIV)$$

wherein $Ar^{11}$ and Met are as defined before, followed by an appropriate conversion(s) to give compounds of the present invention of Formula (XXI).

With appropriate manipulation and protection of any chemical functionalities, synthesis of the remaining compounds of the Formula (I) is accomplished by methods analogous to those above and to those described in the Experimental section.

All reaction intermediates and products so far described can be purified by well-known methods such as recrystallization, reprecipitation, partition procedures, normal- or reverse-phase chromatography and ion-exchange chromatography.

Now, the endothelin antagonistic properties of the heteroaromatic ring-fused cyclopentene derivatives of the present invention will be described.

Endothelin Binding Inhibition Test (1)

The smooth muscle tissue of porcine aorta was homogenized in a buffer solution of 10 mM MOPS, pH 7.4, at 4° C. by a polytron. To the homogenate, sucrose was added to a concentration of 20%, and the mixture was centrifuged at 1,000×g for 15 minutes, and the supernatant was further centrifuged at 10,000×g for 15 minutes. The supernatant thereof was further centrifuged at 90,000×g for 40 minutes. The membrane precipitate thereby obtained was suspended in a buffer solution of 5 mM HEPES/Tris, pH 7.4, at a concentration of 25 mg/ml.

Then, 16 μl of this membrane suspension was added to 340 μl of 50 mM tris/HCl buffer, pH 7.4, containing 10 μl calcium chloride, 10 μM magnesium chloride, 0.1 mM PMSF, 1 μM pepstatin A, 2 μM leupeptin, 1 mM 1,10-phenanthroline and 0.1% bovine serum albumin. To this suspension, 4 μl of (A) endothelin-1 (for nonspecific binding; 0.2 μM as the final concentration), (B) buffer solution A (for total control binding), or (C) a test compound (1.1 μM as the final concentration), was added. Further, to each suspension, 40 μl of $^{125}$I-endothelin-1 (12000–18000 cpm) was added. These mixtures were incubated at 25° C. for 4 hours, then subjected to filtration on a glass filter GF/C and then washed with 5 mM HEPES/Tris, pH 7.4, containing 0.3% bovine serum albumin. Then, the radioactivity trapped by the glass filter was measured, and the $^{125}$I-endothelin-1 binding inhibition D (%) at 1.1 μM of the test compound was determined by the following equation.

$$D(\%) = 100 - \frac{(C) - (A)}{(B) - (A)} \times 100$$

Each test was performed in triplicate.

Compound 2-enantiomer A, a representative compound of the present invention, was found to be very potent inhibitor of endothelin binding to $ET_A$ (93% inhibition at 1.1 μM).

Endothelin Binding Inhibition Test (2)

The cerebellum of porcine was homogenized in a buffer solution of 10 mM MOPS, pH 7.4, at 4° C. by a polytron. To the homogenate, sucrose was added to a concentration of 20%, and the mixture was centrifuged at 1,000×g for 15 minutes, and the supernatant was further centrifuged at 10,000×g for 15 minutes. The supernatant thereof was further centrifuged at 90,000×g for 40 minutes. The membrane precipitate thereby obtained was suspended in a buffer solution of 5 mM HEPES/Tris, pH 7.4, at a concentration of 3.3 mg/ml.

Then, 16 μl of this membrane suspension was added to 340 μl of 50 mM tris/HCl buffer, pH 7.4, containing 10 μl calcium chloride, 10 μM magnesium chloride, 0.1 mM PMSF, 1 μM pepstatin A, 2 μM leupeptin, 1 mM 1,10-phenanthroline and 0.1% bovine serum albumin. To this suspension, 4 μl of (A) endothelin-1 (for nonspecific binding; 0.2 μM as the final concentration), (B) buffer solution A (for total control binding), or (C) a test compound (1.1 μM as the final concentration), was added. Further, to each suspension, 40 μl of $^{125}$I-endothelin-1 (12000–18000 cpm) was added. These mixtures were incubated at 25° C. for 4 hours, then subjected to filtration on a glass filter GF/C and then washed with 5 mM HEPES/Tris, pH 7.4, containing 0.3% bovine serum albumin. Then, the radioactivity trapped by the glass filter was measured, and the $^{125}$I-endothelin-1 binding inhibition D (%) at 1.1 μM of the test compound was determined by the following equation.

$$D(\%) = 100 - \frac{(C) - (A)}{(B) - (A)} \times 100$$

Each test was performed in triplicate.

Compound 2-enantiomer A, a representative compound of the present invention, was found to be very potent inhibitor of endothelin binding to $ET_B$ (80% inhibition at 1.1 μM).

Activities Against Endothelin-Induced Contraction of Isolated Porcine Coronary Arteries The coronary artery of pig was extracted, and a spiral preparation having a width of 1 mm and a length of 10 mm was prepared therefrom. The preparation having the endothelial cells denuded, was hanged in a 5 ml organ bath filled with a Krebs.Heneseleit solution saturated with a gas mixture of 95% $O_2$ and 5% $CO_2$, and a change in the tension was isometrically measured and recorded.

Endothelin-1 was added into the organ bath in a cumulatively increasing manner, whereby the influence of a compound of the present invention to the concentration-response curve for endothelin-1 was examined. The compound was added into the organ bath 20 minutes prior to the addition of endothelin-1.

Compound 2 (10 μM), a representative compound of the present invention, remarkably shifted the concentration-response curves of endothelin-1 to the right and did not affect the maximum response. Further, the compound showed no effects to the isolated coronary artery when applied alone. As is evident from the above, the compound showed remarkable antagonistic activities against endothelin-induced concentration of isolated porcine coronary artery.

Endothelin Binding Inhibition Test (3)

The human neuroblastoma SK-N-MC cells or the human Girardi heart cells purchased from Dainippon Seiyaku (Japan) were cultured in minimal essential medium supplemented with fetal calf serum. The cells were collected and homogenized in 10 mM MOPS buffer (pH 7.4) containing 154 mM NaCl, 10 mM KCl, 0.8 mM $CaCl_2$ and 20% sucrose at 4° C. using a polytron homogenizer. The homogenate was then centrifuged at 1,000×g for 15 minutes. The supernatant was centrifuged at 100,000×g for 1 hour at 4° C. Then the pellet was washed with 5 mM Hepes/Tris buffer (pH 7.4). The resulting membranes were incubated with [$^{125}$I]endothelin-1 in the presence of each test compound or vehicle (1% dimethyl sulfoxide) in 50 mM Tris/HCl buffer (pH 7.4) containing 0.1 mM phenylmethanesulfonyl fluoride, 1 μM pepstatin, 2 μM leupeptin, 1 mM 1,10-phenanthroline, 1 mM EDTA, 10 μM $CaCl_2$, 10 μM $MgCl_2$ and 0.1% BSA in a total volume of 0.4 ml. After 4 hours incubation, cold 5 mM Hepes/Tris buffer (pH 7.4) containing 0.3% BSA (Buffer A) was added to the mixture. Free and bound [$^{125}$I]endothelin-1 were separated by filtration using Whatman GF/C glass fiber filters. After the filtration, the filters were washed with buffer A, and the radioactivity on the filters was measured in a γ counter. Nonspecific binding was determined in the presence of 200 nM endothelin-1.

Percent (%) inhibition of [$^{125}$I]ET-1 specific binding by 1.1 μM of the test compound was determined.

Compound 2-enantiomer A, a representative compound of the present invention, was found to be very potent inhibitor of endothelin binding to $ET_A$ (99% inhibition) and $ET_B$ (80% inhibition) receptors, respectively.

Activities Against Endothelin-Induced Contraction of Isolated Rabbit Iliac Arteries The iliac artery of rabbit was isolated, and a spiral preparation having a width of 1 mm and a length of 10 mm was prepared therefrom. The preparation having the endothelial cells denuded, was placed in a 5 ml organ bath filled with a Krebs.Henseleit solution saturated with a gas mixture of 95% $O_2$ and 5% $CO_2$, and a change in the tension was isometrically measured and recorded.

Endothelin-1 was added into the organ bath in a cumulatively increasing manner, whereby the influence of a compound of the present invention to the concentration-response curve for endothelin-1 was examined. The compound was added into the organ bath 20 minutes prior to the addition of endothelin-1.

Compound 2 (0.1 to 10 μM) remarkably shifted the concentration-response curves of endothelin-1 to the right and did not affect the maximum response. Further, the compound showed no effects to the isolated iliac artery when applied alone. As is evident from the above, the compound showed remarkable antagonistic activities against endothelin-induced concentration of isolated rabbit iliac artery.

Plasma Concentrations After Oral Dosing in Rats

Male SD strain rats (8 weeks, n=3) with a cervical artery cannula were used in this experiment under a fasted condition. Compound 2, which is a representative of the invention, was suspended in 0.5% methylcellulose and administered orally in the stomach with a gavage at a dose of 10 mg/kg. The blood (120 μl) was drained from the cannula just before dosing, and 1 and 8 h after dosing. The plasma was separated by centrifugation (6000 rpm, 10 min, at 4° C.), and a portion (10 μl) was mixed with 40 μl of ethanol and the mixture was centrifugated (10000 rpm, 10 min, at 4° C.) to obtain supernatant. The supernatant (40 μl) was mixed with an equivalent volume of 0.2% trifluoroacetic acid (TFA), and the mixture was subjected to an HPLC assay to determine concentration of Compound 2-enantiomer A which is the active species.

Analytical conditions
analytical column: Chiralcel OD-R (Daicel Chemical, φ4.6 mm×250 mm)
mobile phase: 0.1% TFA-water/0.1% TFA-acetonitrile=75:25
flow rate: 1.0 ml/min
oven temperature: 40° C.
injection volume: 50 μl
detection: absorbance at 276 nm Plasma concentrations of enantiomer A, the active species, were 8.77±3.52 μg/ml and 2.11±0.37 μg/ml at 1 and 8 h, respectively, after oral dosing of Compound 2.

Consequently, the compounds of the present invention were found to be highly orally absorbable and long lasting in the plasma.

Thus, the compounds of the present invention have excellent endothelin antagonistic activities and are useful as vasodilators or bronchodilators in the field of medicines, and they can be drugs for treating hypertension, pulmonary hypertension, Raynaud's disease, acute renal failure, myocardial infarction, angina pectoris, cerebral infarction, cerebral vasospasm, arteriosclerosis, asthma, gastric ulcer, diabetes, restenosis, endotoxin shock endotoxin-induced multiple organ failure or disseminated intravascular coagulation, and/or cyclosporin-induced renal failure or hypertension. When used as drugs for treating such diseases, the compounds of the present invention can be used alone or in combination with other drugs for treatment.

The compounds of the present invention may be used in the form of drug formulations suitable for parenteral administration, oral administration or external administration by mixing them with solid or liquid excipient carriers known in this field. The drug formulations include a liquid formulation such as an injection formulation, an inhalant formulation, a syrup formulation or an emulsion, a solid formulation such as tablets, capsules or granules, and an external drug such as an ointment or a suppository. Further, these drug formulations may contain additives which are commonly employed, such as an adjuvant, a stabilizer, a wetting agent, an emulsifier, an absorption-promoting agent or a surfactant, as the case requires. As the additives, distilled water for injection, physiological saline, Ringer's solution, glucose, sugar syrup, gelatin, vegetable oil, cacao butter, ethylene glycol, hydroxypropyl cellulose, lactose, sucrose, corn starch, magnesium stearate and talc may be mentioned.

The dose of a compound of the present invention as an endothelin antagonist varies depending upon the manner of administration, the age and body weight of the patient and the condition of the patient to be treated. However, a typical administration method for an adult is oral administration or parenteral administration. The daily dose in the case of oral administration to an adult patient is from 0.1 to 100 mg/kg body weight, and the daily dose in the case of parenteral administration is from 0.01 to 10 mg/kg body weight.

The following Examples illustrate the present invention more specifically. It should be understood that the present invention is not limited to these examples alone.

EXAMPLE 1

6-Ethoxycarbonyl-7-(4-methoxyphenyl)-5-(3,4methylenedioxyphenyl)cyclopenteno[1,2-b]pyridine (Compound 1)

(1) 2-(4-Methoxyphenylcarbonyl)-3-pyridine carboxylic acid

To a THF (15 ml) solution of pyridine-2,3-dicarboxylic acid anhydride (1.0 g, 6.7 mmol) was added dropwise a THF solution of 4-methoxyphenylmagnesium bromide (0.89M, 8.0 ml, 7.1 mmol) at −78° C. The reaction mixture was stirred at the same temperature for 1 h and then a saturated aqueous solution of NH$_4$Cl (20 ml) was added to quench the reaction. The reaction mixture was diluted with 1N HCl and extracted with AcOEt. The organic layer was dried over MgSO$_4$, filtered, and concentrated under reduced pressure. The residue was purified by silica gel column chromatography (E. Merck, Kieselgel 60/chloroform:methanol=10:1) to give 2-(4-methoxyphenylcarbonyl)-3-pyridine carboxylic acid (479 mg) as a colorless solid.

(2) 2-(4-Methoxyphenylcarbonyl)-3-pyridylcarbonylmalonic acid diethyl ester

A mixture of 2-(4-methoxyphenylcarbonyl)-3-pyridine carboxylic acid (475 mg, 1.85 mmol) and thionyl chloride (11.0 ml) was stirred at 90° C. for 2 h. The reaction mixture was concentrated under reduced pressure and the residue was dissolved in anhydrous THF. This solution was concentrated under reduced pressure and the residue was dried in vacuo. The resulting residue was dissolved in a mixed solvent of anhydrous THF (60 ml) and anhydrous Et₂O (1.0 ml). To the solution was added diethyl magnesiummalonate (2.0M ether solution, 1.0 ml) which was prepared according to a method described in a literature (J. Am. Chem. Soc., 1946, 68, 1386–1388) and the mixture was stirred at 45° C. for 1.5 h. 1N HCl (10 ml) was added to quench the reaction. The mixture was diluted with water and extracted with AcOEt. The organic layer was dried over MgSO₄, filtered, and concentrated to give 2-(4-methoxyphenylcarbonyl)-3-pyridylcarbonylmalonic acid diethyl ether which was used in the next step without further purification.

(3) 6-Ethoxycarbonyl-7-(4-methoxyphenyl)-5-oxocyclopent-1,4-dieno[1,2-b]pyridine To 2-(4-methoxyphenylcarbonyl)-3-pyridylcarbonylmalonic acid diethyl ester which is prepared in (2) was added a 5% aqueous solution of Na₂CO₃ (10 ml) and the mixture was refluxed for 10 min. After cooling, the supernatant solution was removed by decantation. The aqueous solution was diluted with water and extracted with AcOEt. The residue was suspended in water and the suspension was refluxed. After cooling, the suspension was diluted with brine and extracted with AcOEt. Combined AcOEt layer was dried over MgSO₄, filtered, and concentrated. The residue was purified by silica gel column chromatography (E. Merck, Kieselgel 60/hexane: AcOEt=3:1 to 2:1 to 1:1) to give 6-ethoxycarbonyl-7-(4-methoxyphenyl)-5-oxocyclopent-1,4-dieno[1,2-b]pyridine (215 mg) as an orange oil.

(4) 6-Ethoxycarbonyl-5-hydroxy-7-(4-methoxyphenyl)-5-(3,4-methylenedioxyphenyl)cyclopent-1,4-dieno-[1,2-b]pyridine To a THF (5.0 ml) solution of 6-ethoxycarbonyl-7-(4-methoxyphenyl)-5-oxocyclopent-1,4-dieno-[1,2-b]pyridine (208 mg, 0.67 mmol) was added dropwise 3,4-methylenedioxyphenylmagnesium bromide (1.08M THF solution, 0.8 ml, 0.86 mmol) at 0°–5° C. and the mixture was stirred at the same temperature for 30 min. To the mixture was added 1N HCl (10 ml) to quench the reaction. The mixture was extracted AcOEt and the organic layer was washed with brine, dried over MgSO₄, filtered, and concentrated under reduced pressure. The residue was purified by silica gel column chromatography (E. Merck, Kieselgel 60/hexane:AcOEt=2:1) to give 6-ethoxycarbonyl-5-hydroxy-7-(4-methoxyphenyl)-5-(3,4-methylenedioxyphenyl)cyclopent-1,4-dieno[1,2-b]pyridine (160 mg) as a yellow foam.

(5) 6-Ethoxycarbonyl-7-(4-methoxyphenyl)-5-(3,4-methylenedioxyphenyl)cyclopenteno[1,2-b]pyridine To a ethanol (4.0 ml) solution of 6-ethoxycarbonyl-5-hydroxy-7-(4-methoxyphenyl)-5-(3,4-methylenedioxyphenyl)cyclopent-1,4-dieno[1,2-b]pyridine (130 mg) were added conc. H₂SO₄ (2 drops) and 10% Pd-C (60 mg). The mixture was vigorously stirred at room temperature under an atmospheric pressure of hydrogen. After the reaction completed, the catalyst was removed by Celite-filtration and washed with ethanol. Combined filtrate and washings were washed with sat. NaHCO₃ and brine, dried over Na₂SO₄, filtered and concentrated under reduced pressure. The residue was purified by preparative TLC (E. Merck, Kieselgel 60 F₂₅₄/hexane: AcOEt=1:1) to give 6-ethoxycarbonyl-7-(4-methoxyphenyl)-5-(3,4-methylenedioxyphenyl)cyclopenteno[1,2-b]pyridine (23 mg) as a pale yellow oil.

FAB-MS(m/e): 418(M+H)+
1H-NMR(300 MHz,CDCl₃, δppm):
0.69(3 H,t,J=7.2 Hz),
3.46(2 H,q,J=7.2 Hz),
3.78(3 H,s),
3.88(1 H,t,J=7.6 Hz),
4.70(1 H,d,J=7.6 Hz),
4.79(1 H,d,J=7.6 Hz),
5.94(1 H,d,J=1.5 Hz),
5.95(1 H,d,J=1.5 Hz),
6.76–6.88(5 H,m),
7.17(1 H,dd,J=4.8 Hz,7.6 Hz),
7.34(2 H,d,J=8.9 Hz),
7.52(1 H,d,J=7.6 Hz),
8.51(1 H,d,J=4.8 Hz)

Rf Value: 0.45 (E. Merck, Kieselgel 60 F₂₅₄/hexane:AcOEt=1:1)

EXAMPLE 2

(5RS,6SR,7RS)-6-Carboxy-7-(4-methoxyphenyl)-5-(3,4-methylenedioxyphenyl)cyclopenteno[1,2-b]pyridine (Compound 2).

To a methanol (1.0 ml) solution of 6-ethoxycarbonyl-7-(4-methoxyphenyl)-5-(3,4-methylenedioxyphenyl)cyclopenteno[1,2-b]pyridine (20 mg, 0.048 mmol) which was prepared in Example 1-(5) was added a 4N aqueous solution of NaOH (0.2 ml) and the mixture was stirred at room temperature for 18 h. The reaction mixture was diluted with water, washed with Et₂O and AcOEt, and acidified with 1N HCl. The acidic solution was extracted with AcOEt. The organic layer was washed with brine, dried over Na₂SO₄, filtered, and concentrated under reduced pressure to give 6-carboxy-7-(4-methoxyphenyl)-5-(3,4-methylenedioxyphenyl)cyclopenteno[1,2-b]pyridine (16 mg) as a pale yellow solid. mp: 230°–233° C.(dec.)

FAB-MS(m/e): 390(M+H)+
¹H-NMR(300 MHz,DMSO-d₆, δppm):
3.15(1 H,t,J=10.1 Hz),
3.73(3 H,s),
4.52(1 H,d,J=10.1 Hz),
4.53(1 H,d,J=10.1 Hz),
6.01(2 H,s),
6.77(1 H,dd,J=1.7 Hz,7.7 Hz),
6.84–6.91(4 H,m),
7.15–7.26(4 H,m),
8.33(1 H,d,J=4.1 Hz)

Rf Value: 0.22 (E. Merck, Kieselgel 60 F₂₅₄/chloroform:methanol=10:1)

Compound 2 is a 1:1 mixture of each enantiomer (racemate). These enantiomers can be separated by reverse phase HPLC using a chiral column (Daicel Chemical Chiralcel OD-R, φ4.6 mm×250 mm, flow rate: 1.0 ml/min, 0.1% THF-water/0.1% TFA-acetonitrile=75/25, column temperature: 40° C.).

Retention Time
Compound 2-enantiomer A: 9.8 min
Compound 2-enantiomer B: 12.1 min Each Compound in the following Examples 3–18 was prepared as the same manner described in Examples 1 and 2.

EXAMPLE 3

6-Ethoxycarbonyl-5,7-diphenylcyclopenteno[1,2-b]pyridine

EXAMPLE 4

(5RS,6SR,7RS)-6-Carboxy-5,7-diphenylcyclopenteno[1,2-b]pyridine

EXAMPLE 5

6-Ethoxycarbonyl-5,7-di(4-methoxyphenyl)cyclopenteno[1,2-b]pyridine

EXAMPLE 6

(5RS,6SR,7RS)-6-Carboxy-5,7-di(4-methoxyphenyl)-cyclopenteno[1,2-b]pyridine
High Resolution FAB-MS(m/e,$(C_{23}H_{21}O_4N+H)+$):
Calcd: 376.1549 Found: 376.1536
$^1$H-NMR(300 MHz,CDCl$_3$, δppm):
3.33(1 H,dd,J=9.6 Hz,10.0 Hz),
3.79(3 H,s),
3.82(3 H,s),
4.63(1 H,d,J=9.6 Hz),
4.71(1 H,d,J=9.6 Hz),
6.89(2 H,d,J=8.8 Hz),
6.90(2 H,d,J=8.8 Hz),
7.12(1 H,dd,J=4.6 Hz,8.6 Hz),
7.19(2 H,d,J=8.8 Hz),
7.20(2 H,d,J=8.8 Hz),
7.21–7.30(1 H,m),
8.46(1 H,dd,J=1.4 Hz,4.6 Hz)
Rf Value: 0.29 (E. Merck, Kieselgel 60 F$_{254}$/chloroform:methanol=10:1)

EXAMPLE 7

6-Ethoxycarbonyl-5,7-di(3,4-methylenedioxyphenyl)cyclopenteno[1,2-b]pyridine

EXAMPLE 8

(5RS,6SR,7RS)-6-Carboxy-5,7-di(3,4-methylenedioxyphenyl)cyclopenteno[1,2-b]pyridine

EXAMPLE 9

6-Ethoxycarbonyl-5-(4-methoxyphenyl)-7-(3,4-methylenedioxyphenyl)cyclopenteno[1,2-b]pyridine

EXAMPLE 10

(5RS,6SR,7RS)-6-Carboxy-5-(4-methoxyphenyl)-7-(3,4-methylenedioxyphenyl)cyclopenteno[1,2-b]pyridine mp: 195°–205° C.
High Resolution FAB-MS(m/e,$(C_{23}H_{19}NO_5+H)+$):
Calcd: 390.1341 Found: 390.1338
$^1$H-NMR(300 MHz,CDCl$_3$, δppm):
3.30(1 H,dd,J=9.8 Hz,10.1 Hz),
3.82(3 H,s),
4.61(1 H,d,J=9.7 Hz),
4.68(1 H,d,J=10.1 Hz),
5.92(2 H,s),
6.68(1 H,d,J=1.3 Hz),
6.74(1 H,dd,J=1.3 Hz,7.9 Hz),
6.79(1 H,d,J=7.9 Hz),
6.90(2 H,d,J=8.8 Hz),
7.13(1 H,dd,J=4.9 Hz,7.7 Hz),
7.19(2 H,d,J=8.8 Hz),
7.28(1 H,dd,J=1.6 Hz,7.7 Hz),
8.48(1 H,dd,J=1.6 Hz,4.9 Hz)
Rf Value: 0.25 (E. Merck, Kieselgel 60 F$_{254}$/chloroform:methanol=20:1)

EXAMPLE 11

6-Ethoxycarbonyl-7-(4-methoxyphenyl)-5-phenylcyclopenteno[1,2-b]pyridine

EXAMPLE 12

(5RS,6SR,7RS)-6-Carboxy-7-(4-methoxyphenyl)-5-phenylcyclopenteno[1,2-b]pyridine
High Resolution FAB-MS(m/e,$(C_{22}H_{19}NO_3+H)+$):
Calcd: 346.1443 Found: 346.1444
$^1$H-NMR(300 MHz,CDCl$_3$, δppm):
3.38(1 H,t,J=9.8 Hz),
3.78(3 H,s),
4.68(1 H,d,J=9.8 Hz),
4.73(1 H,d,J=9.8 Hz),
6.89(2 H,d,J=8.8 Hz),
7.12(1 H,dd,J=4.9 Hz,8.6 Hz),
7.19(2 H,d,J=8.8 Hz),
7.20–7.40(6 H,m),
8.47(1 H,dd,J=1.5 Hz,4.9 Hz)
Rf Value: 0.36 (E. Merck, Kieselgel 60 F$_{254}$/chloroform:methanol=10:1)

EXAMPLE 13

6-Ethoxycarbonyl-5-(4-methoxyphenyl)-7-phenylcyclopenteno[1,2-b]pyridine

EXAMPLE 14

(5RS,6SR,7RS)-6-Carboxy-5-(4-methoxyphenyl)-7phenylcyclopenteno[1,2-b]pyridine

EXAMPLE 15

6-Ethoxycarbonyl-7-(3,4-methylenedioxyphenyl)-5phenylcyclopenteno[1,2-b]pyridine

EXAMPLE 16

(5RS,6SR,7RS)-6-Carboxy-7-(3,4-methylenedioxyphenyl)-5-phenylcyclopenteno[1,2-b]pyridine

EXAMPLE 17

6-Ethoxycarbonyl-5-(3,4-methylenedioxyphenyl)-7phenylcyclopenteno[1,2-b]pyridine

EXAMPLE 18

5RS,6SR,7RS)-6-Carboxy-5-(3,4-methylenedioxyphenyl)-7-phenylcyclopenteno[1,2-b]pyridine
High Resolution FAB-MS(m/e,$(C_{22}H_{17}NO_4+H)+$):
Calcd: 360.1236 Found: 360.1225
$^1$H-NMR(300 MHz,CDCl$_3$, δppm):
3.35(1 H,t,J=9.7 Hz),
4.63(1 H,d,J=9.7 Hz),
4.75(1 H,d,J=9.7 Hz),
5.97(2 H,s),
6.72(1 H,d,J=1.7 Hz),
6.77(1 H,dd,J=1.7 Hz,8.0 Hz),
6.81(1 H,d,J=8.0 Hz),
7.14(1 H,dd,J=5.5 Hz,8.3 Hz),
7.20–7.40(6 H,m),
8.48(1 H,dd,J=1.7 Hz,5.5 Hz)
Rf Value: 0.47 (E. Merck, Kieselgel 60 F$_{254}$/chloroform:methanol=10:1)

Each Compound in the following Examples 19 and 20 was prepared using pyridine-3,4-dicarboxylic acid anhydride instead of pyridine-2,3-dicarboxylic acid anhydride as a starting material in the same manner described in Examples 1 and 2.

EXAMPLE 19

(5RS,6SR,7RS)-6-Carboxy-5-(4-methoxyphenyl)-7-(3,4-methylenedioxyphenyl)cyclopenteno[1,2-c]pyridine mp: 190°–192° C.

High Resolution FAB-MS(m/e,($C_{23}H_{19}NO_5$+H)+): Calcd: 390.1341 Found: 390.1354

$^1$H-NMR(300 MHz,DMSO-$d_6$, δppm):
3.18(1 H,t,J=10.2 Hz),
3.75(3 H,s),
4.54(1 H,d,J=10.2 Hz),
4.60(1 H,d,J=10.2 Hz),
6.02(2 H,s),
6.79–6.82(2 H,m),
6.89(1 H,s),
6.89–6.94(1 H,m),
6.93(2 H,d,J=8.4 Hz),
7.23(2 H,d,J=8.4 Hz),
8.00(1 H,s),
8.38(1 H,d,J=4.8 Hz),
12.41(1 H,s)

Rf Value: 0.49 (E. Merck, Kieselgel 60 $F_{254}$/methylene chloride:methanol=8:1)

EXAMPLE 20

(5RS,6SR,7RS)-6-Carboxy-7-(4-methoxyphenyl)-5-(3,4-methylenedioxyphenyl)cyclopenteno[2-c]pyridine mp: 187° C.(dec)

High Resolution FAB-MS(m/e,($C_{23}H_{19}NO_5$+H)+): Calcd: 390.1341 Found: 390.1347

$^1$H-NMR(300 MHz,DMSO-$d_6$, δppm):
3.18(1 H,t,J=10.6 Hz),
3.76(3 H,s),
4.55(1 H,d,J=10.6 Hz),
4.59(1 H,d,J=10.6 Hz),
6.01(2 H,s),
6.79(1 H,dd,J=1.7 Hz,8.1 Hz),
6.82–6.90(3 H,m),
6.93(2 H,d,J=8.5 Hz),
7.26(2 H,d,J=8.5 Hz),
7.96(1 H,s),
8.38(1 H,d,J=4.6 Hz)

Each Compound in the following Examples 21–24 was prepared using the corresponding 6-substituted pyridine-2,3-dicarboxylic acid anhydride as a starting material in the same manner described in Examples 1 and 2.

EXAMPLE 21

(5RS,6SR,7RS)-6-Carboxy-7-(4-methoxyphenyl)-5-(3,4-methylenedioxyphenyl)-2-propoxycyclopenteno[1,2-b]pyridine High Resolution FAB-MS(m/e,($C_{26}H_{25}NO_6$+H)+): Calcd: 448.1760 Found: 448.1778

$^1$H-NMR(300 MHz,CDCl$_3$, δppm):
0.94(3 H,t,J=7.2 Hz),
1.68(2 H,sext,J=7.2 Hz),
3.21(1 H,t,J=9.3 Hz),
3.81(3 H,s),
4.00–4.18(2 H,m),
4.51(1 H,d,J=9.3 Hz),
4.64(1 H,d,J=9.3 Hz),
5.94(2 H,s),
6.56(1 H,d,J=8.0 Hz),
6.70(1 H,s),
6.71–6.80(2 H,m),
6.87(2 H,d,J=8.7 Hz),
7.17(1 H,d,J=8.0 Hz),
7.19(2 H,d,J=8.7 Hz)

Rf Value: 0.44 (E. Merck, Kieselgel 60 $F_{254}$/chloroform:methanol=20:1)

EXAMPLE 22

(5RS,6SR,7RS)-6-Carboxy-7-(4-methoxyphenyl)-5-(3,4-methylenedioxyphenyl)-2-methylcyclopenteno[1,2-b]pyridine mp: 192°–194° C.

FAB-MS(m/e,($C_{24}H_{21}NO_5$+H)+):404

$^1$H-NMR(300 MHz,DMSO-$d_6$, δppm):
2.35(3 H,s),
3.08(1 H,t,J=10.0 Hz),
3.74(3 H,s),
4.46(2 H,t,J=10.0 Hz),
6.00(2 H,s),
6.75(1 H,dd,J=1.6 Hz,8.0 Hz),
6.81(1 H,d,J=1.6 Hz),
6.87–6.91(3 H,m),
7.04(1 H,d,J=7.8 Hz),
7.11–7.17(3 H,m)

Rf Value: 0.29 (E. Merck, Kieselgel 60 $F_{254}$/chloroform:methanol=20:1)

EXAMPLE 23

(5RS,6SR,7RS)-2-Butyl-6-carboxy-7-(4-methoxyphenyl)-5-(3,4-methylenedioxyphenyl)cyclopenteno[1,2-b]pyridine

EXAMPLE 24

(5RS,6SR,7RS)-6-Carboxy-2-ethylaminomethyl-7-(4-methoxyphenyl)-5-(3,4-methylenedioxyphenyl)cyclopenteno[1,2-b]pyridine

EXAMPLE 25

(5RS,6SR,7RS)-6-Carboxy-7-(4-methoxyphenyl)-5-(3,4-methylenedioxyphenyl)cyglopenteno[1,2-b]pyridine N-oxide To a chloroform-methanol (10:1) solution (2.8 ml) of (5RS,6SR,7RS)-6-carboxy-7-(4-methoxyphenyl)-5-(3,4methylenedioxyphenyl)cyclopenteno[1,2-b]pyridine (27.3 mg, 0.0701 mmol) which was prepared in Example 2 was added mCPBA (24.1 mg, 0.14 mmol) at room temperature and the mixture was stirred at the same temperature for 9 h. The reaction mixture was concentrated under reduced pressure and the residue was purified by preparative TLC (E. Merck Kieselgel 60 $F_{254}$/chloroform:methanol:acetic acid=30:1:1) to give a solid, which was partitioned between dichloromethane (20 ml) and water (2 ml). The organic layer was dried over Na$_2$SO$_4$, filtered, and concentrated under reduced pressure to give (5RS,6SR,7RS)-6-carboxy-7-(4-methoxyphenyl)-5-(3,4-methylenedioxyphenyl)cyclopenteno[1,2-b]pyridine N-oxide (21.9 mg) as a pale purple powder. mp: 130°–134° C.

FAB-MS(m/e,($C_{23}H_{19}NO_6$+H)+): 406

$^1$H-NMR(300 MHz,CDCl$_3$, δppm):
3.24(1 H,t,J=5.1 Hz),
3.77(3 H,s),
4.87(1 H,d,J=5.1 Hz),
5.01(1 H,d,J=5.1 Hz),
5.91(2 H,s),
6.65–6.61(2 H,m),
6.67–6.73(1 H,m),
6.82–6.88(2 H,m),
7.10–7.16(2 H,m),
7.23(1 H,d,J=7.8 Hz),
7.31(1 H,dd,J=6.4 Hz,7.8 Hz),
8.20(1 H,d,J=6.4 Hz)

Rf Value: 0.28 (E. Merck, Kieselgel 60 F$_{254}$/chloroform:methanol:acetic acid=30:1:1)

EXAMPLE 26

(5RS,6SR,7RS)-6-Carbamoyl-7-(methoxyphenyl)-5-(3,4-methylenedioxyphenyl)cyclopenteno[1,2-b]pyridine (5RS,6SR,7RS)-6-carboxy-7-(4-methoxyphenyl)-5-(3,4-methylenedioxyphenyl)cyclopenteno[1,2-b]pyridine (27.3 mg, 0.0701 mmol) which was prepared in Example 2, HOBT.H$_2$O (10.7 mg, 0.0700 mmol) and ammonium chloride (7.5 mg, 0.14 mmol) were suspended in DMF (0.70 ml). To the suspension were added EDCI.HCl (16.1 mg, 0.084 mmol) and TEA (20 μl, 0.14 mmol) at 0°–5° C. The resulting mixture was stirred at room temperature for 3.5 h. Dichloromethane (0.70 ml) was added to the suspension and the mixture was additionally stirred at room temperature for 1.5 h. The reaction mixture was concentrated under reduced pressure and the residue was dissolved in AcOEt. The solution was washed with water (2 ml) and brine (2 ml), dried over Na$_2$SO$_4$, filtered, and concentrated under reduced pressure. The residue was purified by preparative TLC (E. Merck Kieselgel 60 F$_{254}$/chloroform:methanol=10:1) to give (5RS,6SR,7RS)-6-carbamoyl-7-(4-methoxyphenyl)-5-(3,4-methylenedioxyphenyl)cyclopenteno[1,2-b]pyridine (25.5 mg) as a colorless powder. mp: 200°–203° C.

FAB-MS(m/e,(C$_{23}$H$_{20}$N$_2$O$_4$+H)+): 389
1H-NMR(300 MHz,CDCl$_3$, δppm):
3.01(1 H,t,J=10.1 Hz),
3.80(3 H,s),
4.67(1 H,d,J=10.1 Hz),
4.69(1 H,d,J=10.1 Hz),
4.91(1 H,brs),
5.23(1 H,brs),
5.94–6.00(2 H,m),
6.72–6.74(1 H,m),
6.79–6.82(2 H,m),
6.88–6.94(2 H,m),
7.09–7.15(1 H,m),
7.18–7.23(2 H,m),
7.28–7.34(1 H,m),
8.44–8.48(1 H,m)

Rf Value: 0.66 (E. Merck, Kieselgel 60 F$_{254}$/chloroform:methanol=10:1)

EXAMPLE 27

(5RS,6SR,7RS)-6-Methanesulfonylaminocarbonyl-7-(4-methoxyphenyl)-5-(3,4-methylenedioxyphenyl)cyclopenteno[1,2-b]pyridine (5RS,6SR,7RS)-6-carboxy-7-(4-methoxyphenyl)-5-(3,4methylenedioxyphenyl)cyclopenteno[1,2-b]pyridine (23.4 mg, 0.0601 mmol) which was prepared in Example 2, methanesulfonic amide (14.4 mg, 0.151 mmol), and DMAP (8.8 mg, 0.72 mmol) were dissolved in DMF (0.60 ml). To the solution was added EDCI.HCl (40.4 mg, 0.21 mmol) at 0°–5° C. The resulting mixture was stirred at room temperature for 78 h. The solvent was removed in vacuo and the residue was partitioned between AcOEt-H$_2$O. The aqueous layer was extracted with AcOEt. The combined organic layer was dried over Na$_2$SO$_4$, filtered, and concentrated under reduced pressure. The residue was purified by preparative TLC (E. Merck Kieselgel 60 F$_{254}$/chloroform:methanol=10:1) to give (5RS,6SR,7RS)-6-methanesulfonylaminocarbonyl-7-(4-methoxyphenyl)-5-(3,4-methylenedioxyphenyl)cyclopenteno[1,2-b]pyridine (17.0 mg) as a colorless powder. mp: 113°–118° C.

FAB-MS(m/e,(C$_{24}$H$_{22}$N$_2$O$_6$S+H)+): 467
1H-NMR(300 MHz,CDCl$_3$, δppm):
3.06(1 H,t,J=10.1 Hz),
3.21(3 H,s),
3.81(3 H,s),
4.69(2 H,d,J=10.0 Hz),
5.95–6.05(2 H,m),
6.68–6.86(3 H,m),
6.90–6.98(2 H,m),
7.12–7.16(1 H,m),
7.16–7.22(2 H,m),
7.28–7.34(1 H,m),
8.44–8.50(1 H,m)

Rf Value: 0.58 (E. Merck, Kieselgel 60 F$_{254}$/chloroform:methanol=10:1)

EXAMPLE 28

(5RS,6SR,7RS)-6-(4-Isopropylbenzenesulfonylaminocarbonyl)-7-(4-methoxyphenyl)-5-(3,4-methylenedioxyphenyl)cyclopenteno[1,2-b]pyridine This compound was prepared using 4-isopropylbenzenesulfonamide in the same manner described in Example 27. mp: 104°–110° C.

FAB-MS(m/e,(C$_{32}$H$_{30}$N$_2$O$_6$S+H)+): 571
1H-NMR(300 MHz,CDCl$_3$, δppm):
1.31(6 H,d,J=6.9 Hz),
2.94(1 H,t,J=10.2 Hz),
3.04(1 H,sept,J=6.9 Hz),
3.82(3 H,s),
4.51(1 H,d,J=10.2 Hz),
4.54(1 H,d,J=10.2 Hz),
5.95–6.02(2 H,m),
6.57(1 H,d,J=1.7 Hz),
6.62(1 H,dd,J=1.7 Hz,8.0 Hz),
6.77(1 H,d,J=8.0 Hz),
6.84–6.92(2 H,m),
6.96–7.04(2 H,m),
7.08–7.14(1 H,m),
7.24–7.30(1 H,m),
7.40–7.46(2 H,m),
7.87–7.93(2 H,m),
8.42–8.46(1 H,m)

Rf Value: 0.69 (E. Merck, Kieselgel 60 F$_{254}$/chloroform:methanol=10:1)

EXAMPLE 29

6-Carboxy-5-hydroxy-7-(4-methoxyphenyl)-5-(3,4-methylenedioxyphenyl)cyclopent-1,4-dieno[1,2-b]pyridine The title compound was prepared using 6-ethoxycarbonyl-5-hydroxy-7-(4-methoxyphenyl)-5-(3,4-methylenedioxyphenyl)cyclopent-1,4-dieno[1,2-b]pyridine which was prepared in Example 1-(4) in the same manner described in Example 2.

1H-NMR(300 MHz,CDCl$_3$, δppm):
3.88(3 H,s),
5.90–5.95(2 H,m),
6.74(1 H,d,J=8.1 Hz),
6.97(1 H,d,J=2.2 Hz),
7.00–7.05(3 H,m),
7.16(1 H,dd,J=4.9 Hz,7.6 Hz),
7.57(1 H,dd,J=1.5 Hz,7.6 Hz),
8.55(1 H,dd,J=1.5 Hz,4.9 Hz)

EXAMPLE 30

(5RS,6SR,7RS)-6-Carboxy-7-(2-carboxymethoxy-4-methoxyphenyl)-5-(3,4-methylenedioxyphenyl)cyclopenteno[1,2-b]pyridine (1) 2-(2-Benzyloxy-4-methoxyphenylcarbonyl)-3-pyridine carboxylic acid To a THF (20 ml) solution of pyridine-2,3-dicarboxylic acid anhydride (1.92 g, 12.9 mmol) was added a THF solution of 2-benzyloxy-4-methoxyphenyllithium (10 ml), which was prepared from 2-benzyloxy-4-methoxyphenyl bromide (3.77 g, 12.9 mmol) and BuLi (1.6M hexane solution, 8.85 ml, 14.2 mmol) at $-78°$ C., at $-78°$ C. over a period of 5 min. The temperature of the mixture was raised to room temperature and the mixture was additionally stirred at the same temperature for 2 h. The reaction mixture was concentrated under reduced pressure and the residue was partitioned between 1N HCl and AcOEt. The organic layer was washed with 1N HCl dried over $Na_2SO_4$, filtered, and concentrated under reduced pressure. The residue was dissolved in 1N NaOH and the solution was washed with AcOEt and chloroform. The aqueous layer was acidified with conc. HCl and extracted with AcOEt. The organic layer was washed with 1N HCl and brine, dried over $Na_2SO_4$, filtered, and concentrated under reduced pressure. The residual solid was recrystallized from is chloroform-ether to give 2-(2-benzyloxy-4-methoxyphenylcarbonyl)-3-pyridine carboxylic acid (2,03 g) as a colorless solid.

(2) 6-Ethoxycarbonyl-7-(2-hydroxy-4-methoxyphenyl)-5-(3,4-methylenedioxyphenyl)cyclopenteno[1,2-b]pyridine The title compound was prepared using 2-(2-benzyloxy-4-methoxyphenylcarbonyl)-3-pyridine carboxylic acid which was prepared in (1), in the same manner described in Example 1-(2)-(5).

(3) 6-Ethoxycarbonyl-7-(2-ethoxycarbonylmethoxy-4-methoxyphenyl)-5-(3,4-methylenedioxyphenyl)cyclopenteno[1,2-b]pyridine To a DMF (1 ml) solution of 6-ethoxycarbonyl-7-(2-hydroxy-4-methoxyphenyl)-5-(3,4-methylenedioxyphenyl)cyclopenteno[1,2-b]pyridine (15 mg, 0.035 mmol) was added a DMF (1.0 ml) suspension of NaH (1.60 mg, 0.040 mmol) at 0°–5° C. The mixture was stirred at 0°–5° C. for 30 min, and at room temperature for 30 min. To the solution was added ethyl bromoacetate (5.74 μl, 0.052 mmol). The mixture was stirred at room temperature for 12 h and then at 50° C. for 3.5 h. 1N HCl was added to the solution and the mixture was partitioned between chloroform and water. The organic layer was washed with 1N HCl, sat. $NaHCO_3$ and brine, dried over $Na_2SO_4$, filtered, and concentrated under reduced pressure. The residue was purified by preparative TLC (E. Merck Kieselgel 60 $F_{254}$/hexane: AcOEt=1:1) to give 6-ethoxycarbonyl-7-(2-ethoxycarbonylmethoxy-4-methoxyphenyl)-5-(3,4-methylenedioxyphenyl)cyclopenteno[1,2-b]pyridine (8.8 mg) as a pale yellow solid.

(4) To a methanol (0.5 ml) solution of 6-ethoxycarbonyl-7-(2-ethoxycarbonylmethoxy-4-methoxyphenyl)-5-(3,4-methylenedioxyphenyl)cyclopenteno[1,2-b]pyridine (8.8 mg, 0.017 mmol) was added 4N NaOH (41.4 μl, 0.17 mmol) and the solution was stirred at room temperature for 3 days. The reaction mixture was diluted with water and washed with AcOEt. The pH value of the aqueous layer was turned to 2–3 and the aqueous layer was extracted with AcOEt. The organic layer was washed with 1N HCl and brine, dried over $Na_2SO_4$, filtered, and concentrated under reduced pressure. The residue was dried in vacuo to give (5RS,6SR,7RS)-6-carboxy-7-(2-carboxymethoxy-4-methoxyphenyl)-5-(3,4-methylenedioxyphenyl)cyclopenteno[1,2-b]pyridine (4.9 mg) as an orange powder. mp: 154°–156° C.

High Resolution FAB-MS(m/e,($C_{25}H_{21}NO_8$+H)+): Calcd: 464.1345 Found: 464.1356

$^1$H-NMR(300 MHz,$CDCl_3$/$CD_3OD$=4/1,δppm):
3.66(1 H,t,J=10.3 Hz),
3.80(3 H,s),
4.60(2 H,ABq,J=16.4 Hz, Δν=47.0 Hz),
4.67(1 H,d,J=10.3 Hz),
5.10(1 H,d,J=10.3 Hz),
5.97(2 H,s),
6.50(1 H,d,J=2.5 Hz),
6.55(1 H,dd,J=2.5 Hz,8.3 Hz),
6.76(1 H,s),
6.80(2 H,s),
7.18(1 H,d,J=8.3 Hz),
7.28(1 H,dd,J=5.5 Hz,7.7 Hz),
7.48(1 H,td,J=1.4 Hz,7.7 Hz),
8.32(1 H,dd,J=1.4 Hz,5.5 Hz)

Rf Value: 0.24 (E. Merck, Kieselgel 60 $F_{254}$/chloroform:methanol:acetic acid=10:1:1)

EXAMPLE 31

(5RS,6SR,7RS)-6-carboxy-5-(2-carboxymethoxy-4-methoxyphenyl)-7-(3,4-methylenedioxyphenyl)cyclopenteno1,2-c]pyridine The title compound was prepared using pyridine-3,4-dicarboxylic acid anhydride in the same manner described in Example 30.

EXAMPLE 32

(5RS,6SR,7RS)-6-carboxy-7-(2-hydroxy-4-methoxyphenyl)-5-(3,4-methylenedioxyphenyl)cyclopenteno[1,2-b]pyridine The title compound was prepared using 6-ethoxycarbonyl-7-(2-hydroxy-4-methoxyphenyl)-5-(3,4-methylenedioxyphenyl)cyclopenteno[1,2-b]pyridine which was prepared in Example 30-(2) in the same manner described in Example 2.

EXAMPLE 33

(5RS,6SR,7RS)-6-carboxy-7-{2-(2-hydroxyethoxy)-4-methoxyphenyl}-5-(3,4-methylenedioxyphenyl)cyclopenteno-[1,2-b]pyridine The title compound was prepared using 2-(tert-butyldimethylsiloxy)ethylbromide in the same manner described in Examples 30-(3) and (4).

EXAMPLE 34

(5RS,6SR,7RS)-6-carboxy-7-{2-(2-methylaminoethoxy)-4-methoxyphenyl}-5-(3,4-methylenedioxyphenyl)cyclopenteno[1,2-b]pyridine 6-Ethoxycarbonyl-7-{2-(2-hydroxyethoxy)-4-methoxyphenyl}-5-(3,4-methylenedioxyphenyl)cyclopenteno[1,2-b]pyridine which was prepared in Example 33 was converted to the corresponding tosylate according to a conventional method and the tosylate was treated with methylamine. The resulting methylamino derivative was hydrolyzed in the same manner described in Example 2 to give (5RS,6SR,7RS)-6-carboxy-7-{2-(2-methylaminoethoxy)-4-methoxyphenyl}-5-(3,4-methylenedioxyphenyl)cyclopenteno[1,2-b]pyridine.

Each Compound in the following Examples 35–45 was prepared by the procedures given above.

EXAMPLE 35

(5RS,6SR,7RS)-6-Carboxy-2-ethoxymethyl-7-(4-methoxyphenyl)-5-(3,4-methylenedioxyphenyl)cyclopenteno[1,2-b]pyridine

EXAMPLE 36

(5RS,6SR,7RS)-6-Carboxy-7-(4-methoxyphenyl)-5-(3,4-methylenedioxyphenyl)-2-propylcyclopenteno[1,2-b]pyridine

EXAMPLE 37

(5RS,6SR,7RS)-6-Carboxy-2-isobutyl-7-(4-methoxyphenyl)-5,(3,4-methylenedioxyphenyl)cyclopenteno[1,2-b]pyridine

EXAMPLE 38

6-Carboxy-7-hydroxy-7-(4-methoxyphenyl)-5-(3,4-methylenedioxyphenyl)cyclopent-1,3-dieno[1,2-b]pyridine

EXAMPLE 39

6-Carboxy-5-hydroxy-7-(4-methoxyphenyl)-5-(3,4-methylenedioxyphenyl)-2-propylcyclopent-1,4-dieno[1,2-b]pyridine

EXAMPLE 40

(5RS,6SR,7SR)-6-Carboxy-5-hydroxy-7-(4-methoxyphenyl)-5-(3,4-methylenedioxyphenyl)cyclopenteno[1,2-b]pyridine

EXAMPLE 41

(5RS,6SR,7RS)-6-Carboxy-7-(4-hydroxyphenyl)-5-(3,4-methylenedioxyphenyl)cyclopenteno[1,2-b]pyridine

EXAMPLE 42

(5RS,6SR,7RS)-6-Carboxy-7-{4-(2-hydroxyethoxy)phenyl}-5-(3,4-methylenedioxyphenyl)cyclopenteno[1,2-b]pyridine

EXAMPLE 43

(5RS,6SR,7RS)-6-Carboxy-7-{4-(2-methylaminoethoxy)phenyl}-5-(3,4-methylenedioxyphenyl)cyclopenteno[1,2-b]pyridine

EXAMPLE 44

(5RS,6SR,7RS)-6-Carboxy-7-(4-hydroxymethylphenyl)-5-(3,4-methylenedioxyphenyl)cyclopenteno[1,2-b]pyridine

EXAMPLE 45

(5RS,6SR,7SR)-6-Carboxy-5-(3,4-methylenedioxyphenyl)-7-(3-thienyl)cyclopenteno[1,2-b]pyridine

EXAMPLE 46

(5RS,6SR,7RS)-7-(4-methoxyphenyl)-5-(3,4-methylenedioxyphenyl)-6-(2-oxo-3H-1,2,3,5-oxathiadiazol-4-yl)cyclopenteno[1,2-b]pyridine The title compound was prepared using (5RS,6SR,7RS)-6-carbamoyl-7-(4-methoxyphenyl)-5-(3,4-methylenedioxyphenyl)cyclopenteno[1,2-b]pyridine which was prepared in Example 26 as a starting material in a method described in the literature (J, Med. Chem. 1993, 36, 2485-2493).

We claim:

1. A heteroaromatic ring-fused cyclopentene derivative of the formula:

$$\text{(I)}$$

wherein each of $Ar^1$ and $Ar^2$ is independently a phenyl group or a thienyl group wherein an optional hydrogen atom(s) on the aromatic ring may be replaced with 1 to 4 groups selected from the group consisting of a hydroxyl group, a carboxyl group, a $C_1-C_6$ alkoxy carbonyl group, a mono- or di- $C_1-C_6$ alkylaminocarbonyl group, a carbamoyl group, a tetrazol-5-yl group a methylenedioxy group, a $C_1-C_6$ alkoxy group, a $C_1-C_6$ alkyl group and a $C_2-C_6$ alkenyl group (provided that the $C_1-C_6$ alkoxy group, the $C_1-C_6$ alkyl group and the $C_2-C_6$ alkenyl group may be substituted by a hydroxyl group, an amino group, a mono- or di- $C_1-C_6$ alkylamino group, a $C_1-C_6$ alkoxy carbonyl group, a mono- or di- $C_1-C_6$ alkylaminocarbonyl group, a carbamoyl group, a carboxyl group, a tetrazol-5-yl group, a 2-oxo-3H-1,2,3,5-oxathiadiazol-4-yl group, a 2,2-dioxo-3H-1,2,3,5-oxathiadiazol-4-yl group, or a 5-oxo-4H-1,2,4-oxadiazol-3-yl group); each of $R^1$, $R^2$ and is independently a hydrogen atom, a hydroxyl group or a $C_1-C_6$ alkyl group, or $R^1$ and $R^2$, or and $R^2$ and $R^3$ together form a single bond; Y is a group of $-CO-R^4$ (wherein $R^4$ is a hydroxyl group, an amino group, a $C_1-C_6$ alkoxy group, a mono- or di- $C_1-C_6$ alkylamino group, an arylsulfonylamino group wherein an optional hydrogen atom(s) on the aryl ring may be replaced with a $C_1-C_6$ alkyl group, or a $C_1-C_6$ alkylsulfonylamino group which may be substituted by an aryl group on the alkyl moiety), a sulfo group, a phosphono group, a tetrazol-5-yl group a 2-oxo-3H-1,2,3,5-oxathiadiazol-4-yl group, a 2.2-dioxo-3H-1,2,3,5-oxathiadiazol-4-yl group, or a 5-oxo-4H-1,2,4-oxadiazol-3-yl group; and A is a group which forms together with the adjacent carbon-carbon double bond a heteroaromatic ring selected from the group consisting of pyridine, pyrimidine, pyridazine, pyrazine and thiazole (provided that an optional hydrogen atom(s) on the heteroaromatic ring may be replaced with a hydroxyl group, an amino group, a $C_1-C_6$ alkoxy group, a halogen atom, a cyano group, a nitro group, a mono- or di- $C_1-C_6$ alkylamino group, a carboxyl group, a $C_1-C_6$ alkoxycarbonyl group, a $C_1-C_6$ acyl group, an aroyl group, or a $C_1-C_6$ alkyl group, $C_2-C_6$ alkenyl group or $C_2-C_6$ alkynyl group which may be substituted by a $C_1-C_6$ alkoxy group or a $C_1-C_6$ alkylamino group, and a nitrogen atom of said heteroaromatic ring may be oxidized to form an N-oxide group); or a pharmaceutically acceptable salt thereof.

2. A compound of claim 1, wherein each of $Ar^1$ and $Ar^2$ is independently a phenyl group or a thienyl group wherein an optional hydrogen atom(s) on the aromatic ring may be replaced with 1 to 4 groups selected from the group consisting of a hydroxyl group, a methylenedioxy group, a $C_1-C_6$ alkoxy group, a carboxy $C_1-C_6$ alkoxy group, a tetrazol-5-yl $C_1-C_6$ alkoxy group, a 2-oxo-3H-,1,2,3,5-oxathiadiazol-4-yl alkoxy group, a 2,2-dioxo-3H-1,2,3,5-oxathiadiazol-4-yl $C_1-C_6$ alkoxy group, a 5-oxo-4H-1,2,4-oxadiazol-3-yl $C_1-C_6$ alkoxy group, a carboxy $C_1-C_6$ alkyl group, a hydroxy $C_1-C_6$ alkyl group, a hydroxy $C_2$-$C_6$ alkoxy group and a $C_1$-$C_6$ alkylamino $C_2$-$C_6$ alkoxy group, and A is a group which forms together with the adjacent carbon-carbon double bond a substituted or unsubstituted pyridine, pyrimidine, pyridazine, pyrazine or thiazole ring, or said heteroaromatic ring N-oxide.

3. A compound of claim 2, wherein A is a group which forms together with the adjacent carbon-carbon double bond a pyridine ring (provided that an optional hydrogen atom(s) on the pyridine ring may be replaced with a $C_1$-$C_6$ alkoxy group, a $C_1$-$C_6$ alkoxy $C_1$-$C_6$ alkyl group, a mono- or di- $C_1$-$C_6$ alkylamino $C_1$-$C_6$ alkyl group, or $C_1$-$C_6$ alkyl group).

4. A drug for the treatment of disorders such as hypertension, pulmonary hypertension, Raynaud's disease, acute renal failure, myocardial infarction, angina pectoris, cerebral infarction, cerebral vasospasm, arteriosclerosis, asthma, gastric ulcer, diabetes, restenosis, endotoxin shock, endotoxin-induced multiple organ failure or disseminated intravascular coagulation, and/or cyclosporin-induced renal failure or hypertension, which contains a heteroaromatic ring-fused cyclopentene derivative of the formula (I) as defined in claim 1 or a pharmaceutically acceptable salt thereof and an excipient carrier.

5. A method for treating hypertension, pulmonary hypertension, Raynaud's disease, acute renal failure, myocardial infarction, angina pectoris, cerebral infarction, cerebral vasospasm, arteriosclerosis, asthma, gastric ulcer, diabetes, restenosis, endotoxin shock, endotoxin-induced multiple organ failure or disseminated intravascular coagulation, and/or cyclosporin-induced renal failure or hypertension comprising administration to a subject in need thereof in effective amount of a compound of claim 1.

* * * * *